United States Patent
Rogalski

(10) Patent No.: US 6,497,673 B2
(45) Date of Patent: Dec. 24, 2002

(54) ELBOW BRACE WITH MASSAGE BALL AND TOPICAL PRODUCT DISPENSER

(76) Inventor: Roger P. Rogalski, 935 Wintergreen Ave., Gardnerville, NV (US) 89410

( * ) Notice: Subject to any disclaimer, the term of this patent is extended or adjusted under 35 U.S.C. 154(b) by 0 days.

(21) Appl. No.: 09/855,603

(22) Filed: May 16, 2001

(65) Prior Publication Data

US 2002/0173738 A1 Nov. 21, 2002

(51) Int. Cl.$^7$ .................................................. A61F 5/00
(52) U.S. Cl. .............................. 602/20; 602/5; 602/21; 602/60; 602/62; 128/846; 128/869; 128/881; 128/878
(58) Field of Search .............................. 602/20–21, 23, 602/26, 60, 62–63; 128/877, 878, 879, 881, 882, 892, 869, 846

(56) References Cited

U.S. PATENT DOCUMENTS

| | | | |
|---|---|---|---|
| 5,063,913 A | | 11/1991 | Nyi |
| 5,295,951 A | * | 3/1994 | Fareed ........................ 602/62 |
| 5,514,081 A | | 5/1996 | Mann |
| 5,672,150 A | * | 9/1997 | Cox ............................. 602/21 |
| 5,746,707 A | * | 5/1998 | Eck ............................. 602/21 |
| 5,823,981 A | | 10/1998 | Grim et al. |
| 5,979,006 A | * | 11/1999 | Stokes et al. ................. 15/222 |
| 5,987,641 A | * | 11/1999 | Walker ............................ 2/16 |
| 6,056,729 A | * | 5/2000 | Yu et al. ...................... 604/289 |
| 6,064,912 A | | 5/2000 | Kenney |
| 6,110,135 A | | 8/2000 | Madow et al. |
| 6,214,027 B1 | * | 4/2001 | Brossard ..................... 606/201 |
| 6,244,271 B1 | * | 6/2001 | Turner et al. ............... 128/869 |

* cited by examiner

*Primary Examiner*—Michael A. Brown
*Assistant Examiner*—Lalita M. Hamilton

(57) ABSTRACT

The present invention offers a brace for the treatment of tennis elbow and similar muscular disorders whereby both massage therapy and the continuous application of a fluid, topical lotion is provided. The brace is attached to the arm of a wearer such that a massage ball protruding from one end of the brace is in contact with the affected area of the arm such that as the arm is moved the massage ball exerts massaging pressure on the arm while simultaneously transferring a fluid, topical lotion from a fluid reservoir to the affected area of the arm.

13 Claims, 3 Drawing Sheets

ELBOW BRACE WITH MASSAGE BALL AND TOPICAL PRODUCT DISPENSER

BACKGROUND OF THE INVENTION

1. Field of the Invention

The present invention relates to orthotic devices, especially as they relate to sports injuries. More particularly, the invention comprises a brace to aid in the relief of lateral epicondylitis, better known as tennis elbow, or other muscular pains, through support, pressure, massage and the application of topical lotions.

2. Description of the Prior Art

Repetitive motion sports injuries have long been a problem suffered by athletes. One of the most common of sports related repetitive motion injuries is lateral epicondylitis, or tennis elbow. A brace is often used to help reduce the pain and swelling from these injuries, with many variations of braces having been expounded over the years.

U.S. Pat. No. 6,110,135, issued to Stephen R. Madow, et. al., on Aug. 29, 2000, presents an ELBOW BRACE WITH MOVABLE SUPPORT, in which a flexible lamination of Airpreene™, providing heat retention, compression and breathability, lined with Coolmax™, which allows wicks perspiration away from the skin, keeping the area dry. A movable support, external to the flexible lamination, provides specific pressure where needed. By contrast, the present invention provides massaging pressure by the use of a massage ball and also provides continuous application of a topical lotion from a reservoir within the brace.

U.S. Pat. No. 6,064,912, issued to John P. Kenney on May 16, 2000, presents an ORTHOTIC/ELECTROTHERAPY FOR TREATING CONTRACTURES DUE TO IMMOBILITY, wherein a cuff around the upper arm or leg and a cuff around the lower arm or leg are hingedly joined by rigid brace members on each side of the joint. In one embodiment, an optional electrotherapy module has electrodes in both the upper and lower cuffs to provide electrical stimulation to damaged muscles to stimulate healing. The present invention, contains no rigid brace members, but rather provides therapy through a massage ball and topical lotion applicator.

U.S. Pat. No. 6,056,729, issued to Min-Tseng Yu on May 2, 2000, presents an ORNAMENTAL ARTICLE FOR TRANSDERMAL DRUG DELIVERY, in which a bracelet is strung with a plurality of beads, each of which has a chamber for holding a topical medication and a plurality of discharge ports. Yu, however, provides no massage therapy, as does the present invention.

U.S. Pat. No. 5,823,981, issued to Tracy E. Grim, et. al., on Oct. 20, 1998, presents a RESILIENT ORTHOPAEDIC SUPPORT WITH INDEPENDENTLY STRETCHABLE LAYERS, wherein a lamination of an inner, breathable layer provides comfort for the wearer and wicks perspiration away from the body while an outer, compressive layer provides support. In the preferred embodiments, Grim includes a padded aperture in the outer, compressive layer which provides a lesser compression on the patella. Additional lateral support is provided for the knee by semi-rigid stays or hinged brace elements incorporated into the sleeve of the brace. Grim does not incorporate massage therapy, as does the present invention, nor release topical lotions.

U.S. Pat. No. 5,514,081, issued to Donaerl B. Mann on May 7, 1996, presents an ELBOW ORTHOSIS HAVING AN INFLATABLE BLADDER SUPPORT AND METHOD OF USE, wherein a flexible, multi-layered brace element containing an inflatable bladder is fitted to a joint such that when the bladder is inflated the joint is substantially immobilized. In a second embodiment, Mann adds a rigid, angularly adjustable brace element over the flexible brace for additional support. Again, Mann does not provide massage therapy or a lotion applicator, as does the present invention.

U.S. Pat. No. 5,063,913, issued to Franklin H. Nyi on Nov. 12, 1991, presents an ELBOW BRACE AND METHOD FOR PREVENTING OR ATTENUATING TENNIS ELBOW, in which a tubular elastic sleeve member is fitted over the elbow joint to provide constrictive support to the elbow. Incorporated into the material of the elastic sleeve member are two donut shaped shock absorbing elements designed to fit over the medial epicondyle and the lateral epicondyle of the humerous. Additionally, a tubular pressure transmitting element is positioned to contact the extensor digitorum muscle while a second tubular pressure transmitting element is positioned to contact the tendon of the triceps brachii. While Nyi does provide massage action through the pressure transmitting elements, it does not provide active rolling or massage therapy by its fixed tubular device or provide means for the continuous application of a topical lotion, as does the present invention.

None of the above inventions and patents, taken either singly or in combination, is seen to describe the instant invention as claimed.

SUMMARY OF THE INVENTION

Lateral epicondylitis, better known as tennis elbow, is a common complaint not only among tennis players, but others, as well. The pain of this ailment and other muscular pains can often be relieved by massage therapy and the application of topical lotions or salves. The present invention presents a brace which provides the desired massage and accupressure therapy and continuous application of a topical lotion or salve.

Accordingly, it is a principal object of the invention to provide an elbow brace which provides massage and pressure therapy to the affected area.

It is a further object of the invention to provide an elbow brace which continuously applies a topical lotion or salve.

Still another object of the invention is to provide an elbow brace which supports the forearm.

An additional object of the invention is to provide an elbow brace which is easy to wear.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
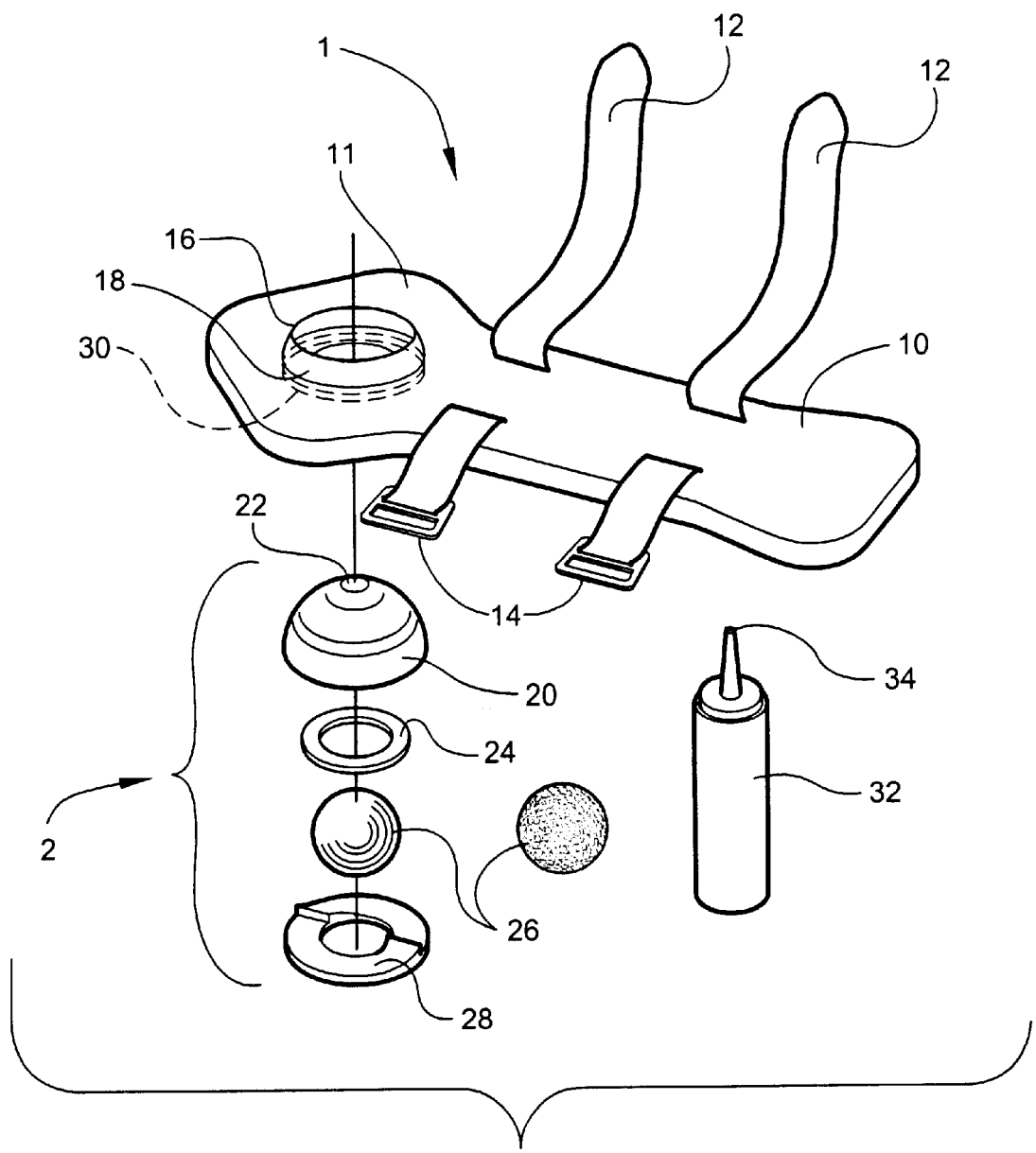
FIG. 1 is an exploded view of the components of the invention.
Figure 2:
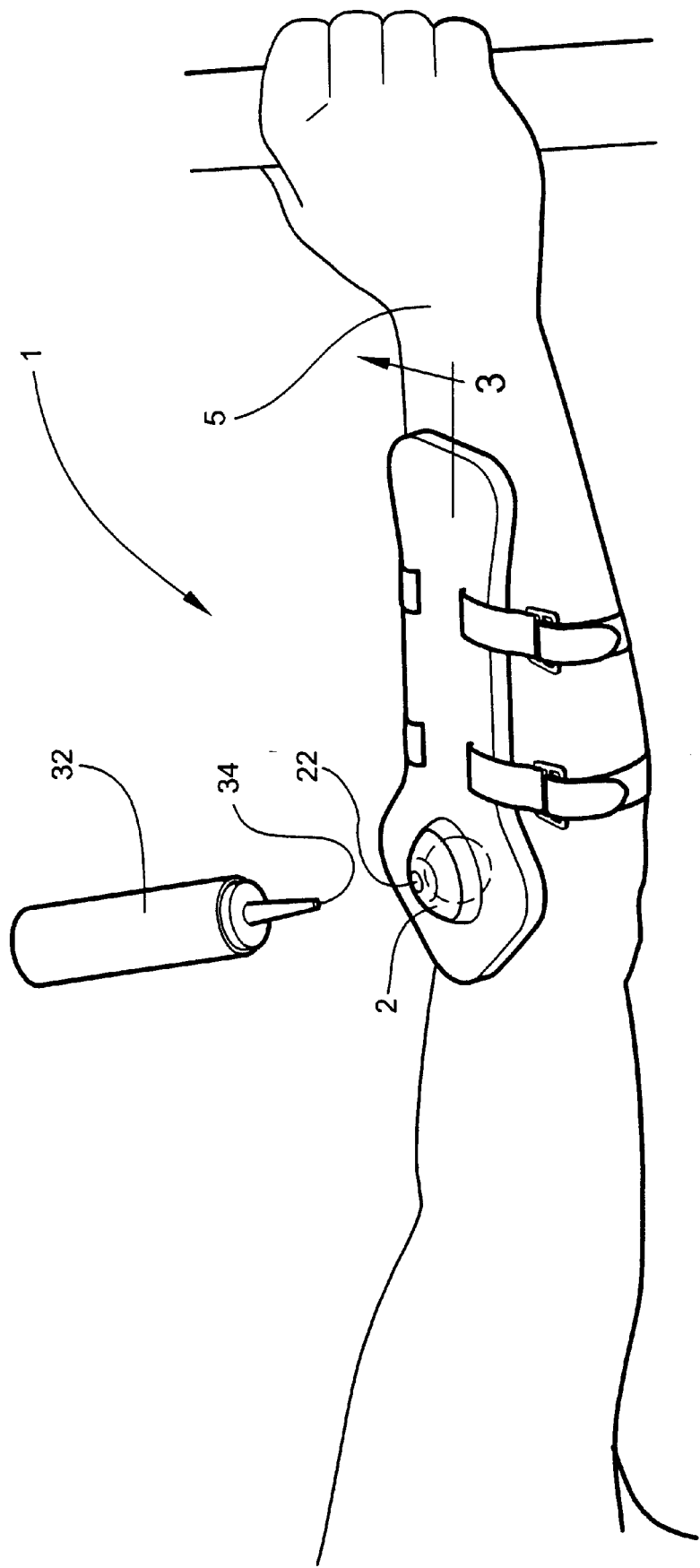
FIG. 2 is an environmental perspective view of the invention as applied to a human elbow.
Figure 3:
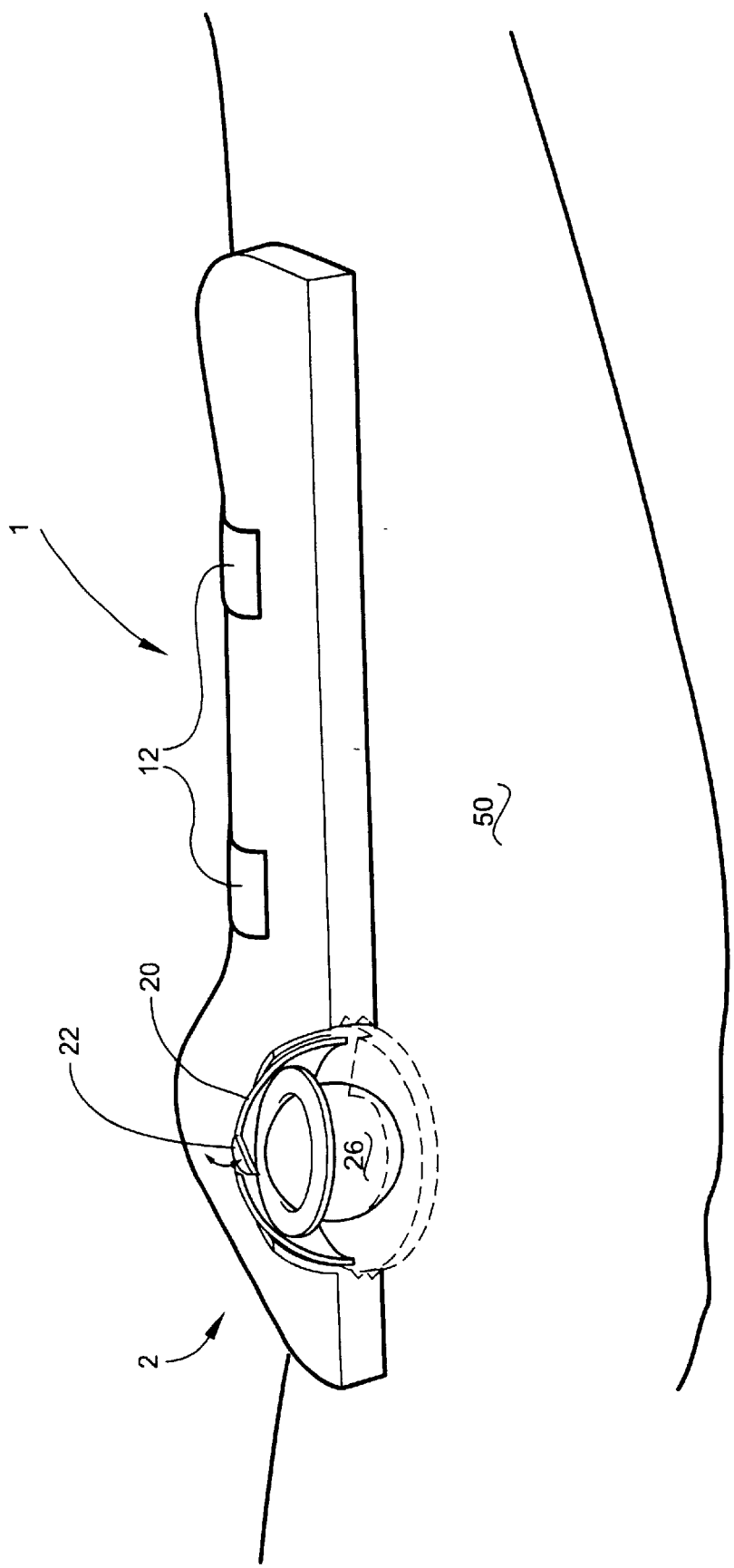
FIG. 3 is an environmental perspective view of the invention, partially cut away, showing contact of the massage ball with the affected area of the elbow.

Referring now to FIGS. 1–3, brace 1 is designed to provide an active massage therapy when applied to an affected area of the arm, generally the elbow.

As illustrated in FIG. 1, the primary structural element of brace 1 is semi-rigid frame 10, which is of a material such as, but not limited to, a polymer, fiberglass, a light weight metal such as aluminum, or other material commonly known in the art for use in braces and splints. Semi-rigid frame 10 has a generally elongate shape, adapted to comfortably lie along a forearm 50, with an expanded, cloverleaf like head 11 at one end. At least two straps 12 are provided for attaching semi-rigid frame 10 to the forearm 50 of a wearer, with its rounded head 11 proximate the elbow. Straps 12 preferably include a fastener of a hook and loop design, such as Velcro®, or alternatively of a strap 12 and buckle 14 design. It would be evident to one skilled in the art that other fastening means could be utilized. It would also be evident that a single strap 12 having a width approximately equal to the elongate portion of semi-rigid frame 10 could be utilized.

Centered in the rounded head 11 of semi-rigid frame 10 is aperture 16. A raised lip 18 surrounds the perimeter of aperture 16 on the upper surface of rounded head 11. Attachment threads 30 surround the perimeter of aperture 16 either on the lower surface of rounded head 11 or on the inner surface of the perimeter of aperture 16. Mounted within aperture 16 is massage ball assembly 2. Raised lip 18 tapers slightly inwardly as it rises from the perimeter of aperture 16 to aid in retaining massage ball assembly 2 in place.

Massage ball assembly 2 is comprised of:
a hollow, hemispherical reservoir 20 having a one-way valve 22 at the upper limit of the hemisphere;
a gasket 24 having an aperture at its center and adapted to fit within the upper region of the interior of hemispherical reservoir 20;
a massage ball 26 constrained within hemispherical reservoir 20 between gasket 24 and protruding from the open bottom of the hemispherical reservoir 20 through an aperture in the center of
a locking ring 28 engaging the threads 30 surrounding the perimeter of aperture 16.

It would be evident to one skilled in the art that a number of different materials would be suitable for the manufacture of the various elements of massage ball assembly 2, such as, but not limited to, a polymer, fiberglass, or a metal. Likewise, massage ball 26 could be of numerous designs, as will be discussed later.

FIG. 2 illustrates brace 1 as it is fitted to the forearm 50 of the wearer. Straps 12 hold semi-rigid frame 10 against forearm 50 such that massage ball 26 is in contact with the affected muscles. The reservoir created by the juxtaposition of hollow hemisphere 20, gasket 24 and massage ball 26 is filled with a fluid, topical lotion by introducing the topical lotion through one-way aperture 22. In a preferred embodiment, a bottle 32 having a nipple 34 contains a fluid, topical lotion. Nipple 34 is introduced into one-way valve 22 and bottle 32 is squeezed, forcing the liquid, topical lotion through one-way valve 22 into the reservoir of ball assembly 2. As the arm is used in normal day to day activities or during athletic activities, the pressure of massage ball 26 against the surface of the arm provides a massaging action to the affected muscles and the fluid, topical lotion is transferred from the reservoir to the affected area of the arm.

As has been stated previously, the design of massage ball 26 may be varied to provide differing benefits. A smooth surfaced ball 26, being in relatively close communication with the aperture of gasket 24 would transfer a limited amount of lotion from reservoir 20 to the affected muscles. A dimpled ball 26, being in a more open communication with the aperture of gasket 24 could transfer a greater amount of lotion from reservoir 20 to the affected muscles. A magnetized steel ball 26 could provide magnetic therapy in addition to the massage therapy provided by balls 26 of other composition. It would be evident that a variety of massage balls 26 could be packaged with each brace 1, or different types of ball 26 could be sold separately, as needed.

It would be obvious that a wide variety of typical applications may be used with the inventive brace 1, the actual material forming no part of the instant invention.

It is to be understood that the present invention is not limited to the embodiments described above, but encompasses any and all embodiments within the scope of the following claims.

What is claimed is:

1. A brace for the treatment of tennis elbow and similar muscular disorders comprising:
a semi-rigid brace frame adapted for attaching to an arm of a wearer and having an aperture proximate one end of said brace frame,
a massage ball adapted to be constrained in said aperture and further adapted to exert a massaging pressure on affected muscles in said arm proximate said massage ball
wherein the assembly of said massage ball and said reservoir comprises:
said massage ball,
a hollow hemisphere forming the housing of said reservoir, said hemisphere adapted to fit through said aperture in said brace frame and having
a one-way valve located in an uppermost portion of said hemisphere, said valve passing one-way from the exterior of said hemisphere to the interior of said hemisphere and adapted to allow passage of a fluid into said reservoir,
a gasket having an aperture at its center and adapted to fit within the upper region of the interior of said hollow hemisphere,
a locking ring having an aperture at its center and threads around its perimeter and adapted to removably communicate with threads at the perimeter of said aperture in said brace frame,
said massage ball protruding through said apertures in said gasket and said locking ring and being constrained between said gasket and said locking ring, and
said assembly being constrained between said brace frame and said locking ring.

2. A brace for the treatment of tennis elbow and similar muscular disorders, as defined in claim 1, wherein said brace frame is composed of one of the materials of the group: a polymer, fiberglass, and a light weight metal.

3. A brace for the treatment of tennis elbow and similar muscular disorders, as defined in claim 1, wherein said massage ball is in fluid communication with a reservoir, said reservoir being adapted to hold and dispense a fluid topical lotion to the surface of said massage ball for transfer to the area of the affected tendons or muscles.

4. A brace for the treatment of tennis elbow and similar muscular disorders, as defined in claim 1, wherein said brace frame is adapted to be attached to an arm of the wearer by at least one strap, said strap adapted to wrap around the arm of the wearer.

5. A brace for the treatment of tennis elbow and similar muscular disorders, as defined in claim 1, wherein said massage ball comprises one of the group of a polymer, fiberglass, and a light metal.

6. A brace for the treatment of tennis elbow and similar muscular disorders, as defined in claim 5, wherein said massage ball comprises at least one characteristic of the group: smooth surfaced, dimpled surfaced, raised stud surfaced, and magnetic.

7. A brace for the treatment of tennis elbow and similar muscular disorders comprising:
   a semi-rigid brace frame adapted to be attached to an arm of a wearer by
      at least two straps, said at least two straps being spaced apart from one another along the length of said brace frame and adapted to wrap around the arm of the wearer,
   said brace frame further comprising:
      an aperture proximate one end of said brace frame, said aperture receiving
         a massage ball assembly further comprising:
            a hollow hemisphere having a one-way valve proximate the upper limit of said hemisphere, said valve passing one-way from the exterior of said hemisphere to the interior of said hemisphere,
            a gasket having an aperture at its center and adapted to fit proximate the upper region of said interior of said hemisphere,
            a massage ball,
            a locking ring having an aperture at its center and adapted to removably communicate with the perimeter of said aperture in said brace frame,
            said massage ball protruding through said apertures in said gasket and said locking ring and being constrained between said gasket and said locking ring,
            said hollow hemisphere, said gasket and said massage ball forming a reservoir for the storage of a fluid, topical lotion, and
            said one-way valve adapted to allow passage of a fluid into said reservoir, and
         said assembly being constrained between said brace frame and said locking ring with said hemisphere protruding through said aperture in said brace frame.

8. A brace for the treatment of tennis elbow and similar muscular disorders, as defined in claim 7, wherein said hollow hemisphere is formed as an integral part of said brace frame at said aperture in said brace frame.

9. A brace for the treatment of tennis elbow and similar musculo-skeletal disorders, as defined in claim 7, wherein said brace frame is composed of one of the group of a polymer, fiberglass, and a light weight metal.

10. A brace for the treatment of tennis elbow and similar muscular disorders, as defined in claim 7, wherein said at least two straps comprise one of the group of flexible hook and loop fastener strips, and flexible straps with buckle fasteners.

11. A brace for the treatment of tennis elbow and similar muscular disorders, as defined in claim 7, wherein said massage ball comprises one of the group of a polymer, fiberglass, and a light metal.

12. A brace for the treatment of tennis elbow and similar muscular disorders, as defined in claim 11, wherein said massage ball comprises at least one characteristic of the group: smooth surfaced, dimpled surface, raised stud surface, and magnetic.

13. A method, using a brace, for the treatment of tennis elbow and similar muscular disorders, comprising:
   providing a brace, said brace comprising:
      a semi-rigid brace frame adapted to be attached to an arm of a wearer by
         at least two straps, said at least two straps being spaced apart from one another along the length of said brace frame and adapted to wrap around the arm of the wearer,
      said brace frame further comprising:
         an aperture proximate one end of said brace frame said aperture receiving
            a massage ball assembly further comprising:
               a hollow, hemisphere having a one-way valve proximate the upper limit of said hemisphere, said valve passing one-way from the exterior of said hemisphere to the interior of said hemisphere,
               a gasket having an aperture at its center and adapted to fit proximate the upper region of said interior of said hemisphere,
               a massage ball,
               a locking ring having an aperture at its center and adapted to removably communicate with the perimeter of said aperture in said brace frame,
               said massage ball protruding through said apertures in said gasket and said locking ring and being constrained between said gasket and said locking ring,
               said hollow hemisphere, said gasket and said massage ball forming a reservoir for the storage of a fluid, topical lotion, and
               said one-way valve being adapted to allow passage of a fluid into said reservoir, and
            said assembly being constrained between said brace frame and said locking ring with said hemisphere protruding through said aperture in said brace frame; and
   said method further comprising:
      attaching said brace to a forearm of a wearer with said at least two straps such that said massage ball is in contact with the affected muscles of the arm,
      introducing a fluid, topical lotion into said reservoir via said one-way valve,
      using said arm in normal manner, thereby causing said massage ball to apply a massage action to said affected muscles of said arm and over time transfers said fluid, topical lotion from said reservoir to said arm.

* * * * *